（12）United States Patent
Hillis et al.

(10) Patent No.: US 9,134,205 B2
(45) Date of Patent: Sep. 15, 2015

(54) SYSTEM AND METHOD FOR REMOVING SURFACE PARTICLES FROM AN OBJECT

(71) Applicant: Elwha LLC, Bellevue, WA (US)

(72) Inventors: Daniel W. Hillis, Encino, CA (US);
Roderick A. Hyde, Redmond, WA (US);
Jordin T. Kare, Seattle, WA (US);
Muriel Y. Ishikawa, Livermore, CA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 422 days.

(21) Appl. No.: 13/623,036

(22) Filed: Sep. 19, 2012

(65) Prior Publication Data

US 2014/0076068 A1 Mar. 20, 2014

(51) Int. Cl.
*G01N 1/22* (2006.01)
*G01N 1/02* (2006.01)

(52) U.S. Cl.
CPC .............. *G01N 1/22* (2013.01); *G01N 1/2202* (2013.01); *G01N 2001/022* (2013.01); *G01N 2001/028* (2013.01)

(58) Field of Classification Search
CPC .................. G01N 2001/022; G01N 2001/024; G01N 1/2202
See application file for complete search history.

(56) References Cited

U.S. PATENT DOCUMENTS

| 5,915,268 | A | | 6/1999 | Linker et al. |
|---|---|---|---|---|
| 5,999,257 | A | | 12/1999 | Myers et al. |
| 6,073,499 | A | * | 6/2000 | Settles ...................... 73/864.81 |
| 6,334,365 | B1 | | 1/2002 | Linker et al. |
| 6,708,572 | B2 | | 3/2004 | Jenkins et al. |
| 6,840,122 | B1 | | 1/2005 | Jenkins et al. |
| 8,339,606 | B2 | | 12/2012 | Howieson |
| 2002/0078767 | A1 | | 6/2002 | Jenkins et al. |
| 2005/0120776 | A1 | | 6/2005 | Jenkins et al. |
| 2006/0081073 | A1 | | 4/2006 | Vandrish et al. |
| 2008/0053252 | A1 | | 3/2008 | Jenkins et al. |
| 2009/0325300 | A1 | | 12/2009 | Clift et al. |
| 2010/0282960 | A1 | | 11/2010 | Clark |
| 2011/0132108 | A1 | | 6/2011 | Novosselov et al. |
| 2014/0076068 | A1 | | 3/2014 | Hillis et al. |
| 2014/0076069 | A1 | | 3/2014 | Hillis et al. |
| 2014/0170735 | A1 | | 6/2014 | Holmes |

OTHER PUBLICATIONS

PCT International Search Report; International App. No. PCT/US2013/060391; Feb. 18, 2014; pp. 1-2.
Cygnus Business Media, "'Puffing' at the Newark Airport", http://www.securityinfowatch.com/news/10578525/puffing-at-the-newark-airport, Jul. 28, 2005, retrieved Sep. 19, 2012, 4 pgs.

(Continued)

*Primary Examiner* — Paul West

(57) ABSTRACT

A fluid jet may be delivered by an outlet to dislodge particles from an object, such as a person. An image sensor may determine a target location on the object for delivering the fluid jet. In some embodiments, the image sensor may locate particles of interest to determine the target location. A steering mechanism may direct the fluid jet, so that it impacts the target location. The dislodged particles may then be captured for analysis. A distraction mechanism may distract the object and/or mask the sound of the fluid jet to prevent the object from realizing the fluid jet has been delivered. Additional substances and/or tags may be delivered by the outlet to the object and/or particles.

38 Claims, 10 Drawing Sheets

(56) References Cited

OTHER PUBLICATIONS

Ron Marsico, "'Puffer' Bomb Screeners a Bust", http://seattletimes.com/html/nationworld/2003744097_puff12.html, Jun. 12, 2007, retrieved Sep. 19, 2012, 6 pgs.

Wikipedia Foundation, Inc., "Explosives Trace-Detection Portal Machine", http://en.wikipedia.org/wiki/Explosives_trace-detection_portal_machine, Apr. 15, 2012, retrieved Sep. 19, 2012, 4 pgs.

"Atmospheric Pressure Photoionization Source"; Agilent Technologies; printed on Jan. 11, 2015; pp. 1-2; located at: http://www.chem.agilent.com/en-US/products-services/Instruments-Systems/Mass-Spectrometry/Atmospheric-Pressure-Photoionization-Source-(APPI)/Pages/gp2294.aspx.

"Visible spectrum"; Wikipedia; printed on Apr. 9, 2015; p. 1; located at: http://en.wikipedia.org/wiki/Visible_spectrum.

* cited by examiner

SYSTEM AND METHOD FOR REMOVING SURFACE PARTICLES FROM AN OBJECT

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None

RELATED APPLICATIONS

U.S. patent application Ser. No. 13/623,041, entitled SYSTEM AND METHOD FOR REMOVING SURFACE PARTICLES FROM AN OBJECT, naming Daniel W. Hillis, Roderick A. Hyde, Jordin T. Kare, Muriel Y. Ishikawa, and Lowell L. Wood, Jr. as inventors, filed 19 Sep. 2012, is related to the present application.

U.S. patent application Ser. No. 13/623,044, entitled SYSTEM AND METHOD FOR REMOVING SURFACE PARTICLES FROM AN OBJECT, naming Daniel W. Hillis, Roderick A. Hyde, Jordin T. Kare, Muriel Y. Ishikawa, and Lowell L. Wood, Jr. as inventors, filed 19 Sep. 2012, is related to the present application.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

TECHNICAL FIELD

This disclosure relates to systems and methods for delivering a fluid jet to remove surface particles from an object.

SUMMARY

Various surface particles may be present on an object. An object with surface particles may be a person, something carried by a person, packages or luggage, clothing, or the like. The surface particles may be substances of interest, and/or information may be gleaned from the surface particles. Thus, it may be desirable to analyze the surface particles to detect particles of interest. Analysis of surface particles may be used for a variety of purposes, such as safety, security, crime detection, and the like. The analysis may be designed to detect explosives, narcotics, harmful biological agents, and the like and/or to identify the object.

Surface particles of interest may be acquired by delivering a dislodging fluid jet to the object and capturing particles dislodged from the object. Analysis may be made more sensitive by capturing particles likely to yield useful information. An image sensor may be used to identify particles of interest and/or locations of interest on the object to be targeted. A dislodging fluid jet may be delivered to dislodge the particles of interest. The dislodging fluid jet may be directed so that it will impact the particles of interest and/or the target location, such as by using a steering mechanism. The dislodged particles may then be captured and analyzed. Additionally, the dislodged particles may be tracked, so, for example, the dislodged particles may be directed in flight and/or captured more easily. Alternatively, the dislodged particles may be tracked and/or analyzed without being captured. Analysis with or without capture may allow the dislodged particles and/or the object to be identified.

It may be desirable in some situations for a person or other object to be unaware that the dislodging fluid jet has been delivered to it. Likewise, it may be desirable to deliver the dislodging fluid jet without intervention by a user or operator. A proximity sensor may detect the presence of the object, and the dislodging fluid jet may be delivered after the object is detected. A distraction and/or masking mechanism may be configured to hinder the person or other object from detecting delivery of the dislodging fluid jet. Additional substances may also be delivered with the dislodging fluid jet, such as to track the object.

BRIEF DESCRIPTION OF THE DRAWINGS

FIG. 5 is a side view of a mechanically controlled outlet for delivering a dislodging fluid jet, a deflecting fluid jet, a capturing fluid jet, or the like.

FIG. 6 is a cross-section view of an outlet for electrically steering a dislodging fluid jet, a deflecting fluid jet, a capturing fluid jet, or the like.

DETAILED DESCRIPTION OF PREFERRED EMBODIMENTS

Figure 1:
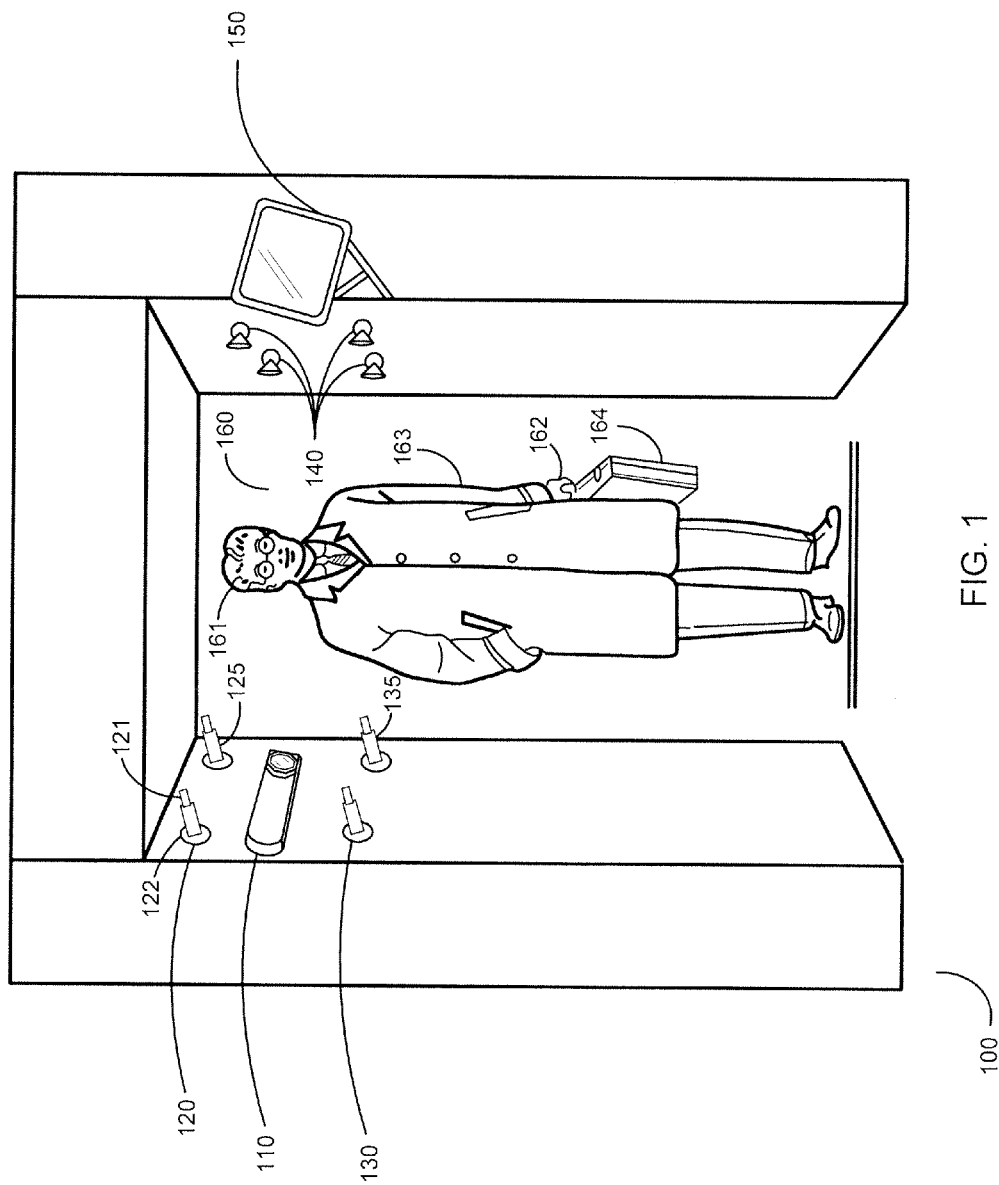
FIG. 1 is a front view of a system for acquiring surface particles from an object for analysis.

Surface particles may be dislodged so that they can be analyzed. Accordingly, a surface particle removal system may deliver a fluid jet to dislodge the surface particles, so they can be captured and/or analyzed. The dislodging fluid jet may be delivered from a first outlet, such as a nozzle. The dislodging fluid jet may be a gas and/or a liquid. For example, a gas fluid jet may be air; air and a distinguishing gas, such as a visible distinguishing gas or a fluorescing distinguishing gas; a noble gas; nitrogen; oxygen; fluorine; carbon dioxide; water vapor; and/or the like. A liquid fluid jet may be water, ethanol, and/or the like. The dislodging fluid jet may be delivered as a continuous stream, in short pulses, and/or as one or more vortex rings. In some embodiments, the first outlet may deliver the dislodging fluid jet continuously and surface particles may be dislodged from passing objects.

The surface particle removal system may determine a target location on the object for delivery of the dislodging fluid jet. The target location may be determined by identifying surface particles of interest on the object. Various particles of interest may be targeted, including skin cells, dust, pollen, bacteria, excreta, lint, and the like. The particles of interest may be identified by using an electromagnetic radiation sensor such as an antenna, a camera, or the like. For example, an image captured by an image sensor, such as a camera, may be compared with one or more reference images to identify particles of interest. The electromagnetic radiation sensor may be configured to detect electromagnetic radiation in the microwave; terahertz; infrared, such as thermal infrared; visible; ultraviolet; and/or x-ray spectrum.

The surface particle removal system may also comprise an electromagnetic radiation emitter to emit electromagnetic radiation at the object. The electromagnetic radiation emitter may comprise a light source, such as a laser, a collimated beam, or the like. The emitted radiation may be in various electromagnetic spectrums, such as infrared, visible, and/or ultraviolet. The particles of interest may be identified based on a response to the emitted radiation detected by the electromagnetic radiation sensor. For example, the particles of interest may be detected using radar. The emitted electromagnetic radiation may be spectral illumination configured to cause a spectral emission from the particles of interest and/or illumination configured to cause fluorescence. A spectrometer or the like may be used to detect spectral emissions of interest with or without illumination. Similarly, fluorescence from particles of interest may be detected with or without illumination. The particles of interest may be identified by detecting spectral emissions or fluorescence of interest in predetermined electromagnetic spectrums.

Instead or in addition, the surface particle removal system may emit ultrasonic waves at the object. An ultrasonic wave detector may detect reflections of the ultrasonic waves off the object or particles of interest. The ultrasonic wave detector may comprise an image sensor configured to generate an image from the ultrasonic waves detected. The image of the detected ultrasonic waves may be compared to a reference image to identify the particles of interest.

A steering mechanism may steer the fluid jet to the target location. The steering mechanism may steer the fluid jet based on information from an image sensor. The image sensor may be configured to image the impact of the dislodging fluid jet at an impact location and/or the target location. The image sensor may determine whether the dislodging fluid jet hit and/or dislodged a particle of interest. The steering mechanism may then steer the dislodging fluid jet based on feedback from the image sensor. If the dislodging fluid jet did not dislodge the particle of interest, the outlet may continue to deliver and/or increase the power of the dislodging fluid jet. If the particle of interest has been dislodged, the outlet may stop delivery of the dislodging fluid jet.

Various steering mechanisms may be used to steer the dislodging fluid jet. For example, the steering mechanism may mechanically steer the dislodging fluid jet, such as by aiming the outlet. The outlet may be aimed with a motor, a robotically movable arm, or the like. A robotically movable arm may comprise a particle capture mechanism. The robotically movable arm may control positioning of the particle capture mechanism. Alternatively or additionally, the particle capture mechanism may be positioned on the robotically movable arm such that the particle capture mechanism will be in the path of the dislodging fluid jet and/or the path of dislodged particles. The steering mechanism may steer the fluid jet in flight by altering the path of the fluid jet in some embodiments. The path of the fluid jet may be altered by delivering a deflecting fluid jet from a second outlet and/or by passing an ionized fluid jet by one or more charged and/or magnetic elements.

A proximity sensor may be configured to detect the object. The first outlet may be configured to deliver the dislodging fluid jet after the object is detected by the proximity sensor. The proximity sensor may be a pressure sensor, such as a piezoelectric sensor, a piezoresistive sensor, a weighing scale, a capacitive load sensor, or the like; a capacitive sensor; an inductive sensor; an electromagnetic radiation sensor, such as an image sensor, an optical sensor, or the like; and/or the like. An electromagnetic radiation sensor may be configured to detect electromagnetic radiation in the microwave; terahertz; infrared, such as thermal infrared; visible; ultraviolet; and/or x-ray spectrum.

The proximity sensor may further comprise an electromagnetic radiation emitter. The emitted radiation may be in various electromagnetic spectrums, such as infrared, visible, and/ or ultraviolet. The electromagnetic radiation emitter may comprise a light source, such as a laser, a collimated beam, or the like. The proximity sensor may be configured to detect obstruction of a beam. Instead or in addition, the proximity sensor may be configured to detect the emitted radiation, such as by detecting reflected radiation. The proximity sensor may comprise radar, lidar, and/or the like. In some embodiments, the proximity sensor may comprise an ultrasonic wave emitter and may be configured to detect the ultrasonic waves.

The proximity sensor may be configured to detect a velocity of the object and/or a distance to the object. The proximity sensor may detect the velocity using the Doppler effect, such as with a Doppler radar, a Doppler lidar, or a Doppler ultrasound; using motion between images of the object; or the like. In some embodiments, the proximity sensor may be configured to predict an arrival time of the object at a delivery region, and the first outlet may be configured to deliver the dislodging fluid jet to the delivery region at the arrival time. Alternatively or additionally, the proximity sensor may be configured to detect the object within a delivery region of the first outlet, and the first outlet may be configured to deliver the dislodging fluid jet when the object is within the delivery region.

Particles of interest may be dislodged from various objects and target locations. The object may be a person, and the target location may be that person's hair or a skin surface on that person. In some embodiments, a predetermined portion of the skin surface may be the target location and/or specific areas of the skin surface may be avoided. Alternatively or additionally, the object may be inanimate, such as clothing, an object carried by a person, or the like. In some embodiments, specific types of clothing may be targeted, including clothing that traps and/or releases particles easily, wool, or the like. Instead or in addition, specific types of clothing may be avoided. The target location may be the entirety of an object and/or a specific portion of the object smaller than the entire object.

Dislodged particles may be tracked and/or analyzed after dislodgement. An image sensor may be used to track the dislodged particles in some embodiments. The image sensor may predict a path of the dislodged particles and/or an arrival time of the dislodged particles at a capture mechanism. A light source, such as a laser, a collimated beam, or the like, may be used to irradiate the dislodged particles. In some embodiments, the light source may be steerable to selectively irradiate the dislodged particles. The image sensor may track the dislodged particles by tracking a fluorescence pattern, a light scattering pattern, spectral emissions, or the like. The dislodged particles may be steered in flight, such as by delivering a capturing fluid jet from the first outlet and/or from a second outlet or the like. The capturing fluid jet may comprise vortex rings in some embodiments. A particle capture mechanism comprising a robotically movable arm may be configured to intercept the dislodged particles being tracked, such as by moving to a sensed location or a predicted location of the dislodged particles.

Identifying characteristics of the dislodged particles may be analyzed in flight by an image sensor or the like. The image sensor may be configured to analyze electromagnetic radiation, such as by using a camera to compare an image of the dislodged particles to a reference. The image sensor may analyze electromagnetic radiation in the infrared spectrum, the visible spectrum, the ultraviolet spectrum, and/or the like. An electromagnetic radiation emitter may emit electromagnetic radiation at the dislodged particles, so the image sensor can detect the response of the dislodged particles to the emitted electromagnetic radiation. The electromagnetic radiation emitter may comprise a light source, such as a laser, a collimated beam, or the like. The image sensor may comprise a spectrometer and/or be configured to detect fluorescent emissions to analyze the dislodged particles. Alternatively or additionally, the image sensor may comprise an ultrasonic wave emitter and may be configured to analyze ultrasonic waves reflected by the dislodged particles, such as by comparing an image of the dislodged particles to a reference.

In some embodiments, the dislodged particles may be captured with a particle capture mechanism. The particle capture mechanism may comprise a filter, an electrostatic precipitator, or the like. Alternatively or additionally, the particle capture mechanism may comprise a gate configured to open upon arrival of the dislodged particles and/or may use suction to capture the dislodged particles. The arrival of the dislodged particles may be determined using continuous tracking of the dislodged particles, intermittent tracking, and/or prediction of the time of arrival. The particle capture mechanism may only be on when the dislodged particles arrive and/or may comprise a shutter or diverter so only the tracked particles are captured. A robotically movable arm may be configured to move or position the particle capture mechanism, so that it may capture the dislodged particles.

The particle capture mechanism may be further configured to analyze the dislodged particles. The particle capture mechanism may be configured to analyze biological characteristics, genetic characteristics, chemical characteristics, radioactive characteristics, fluorescence, spectral emissions, or the like. The particle capture mechanism may comprise a mass spectrometer and/or use electrophoresis to analyze the particles in some embodiments. The particle capture mechanism may analyze radioactive characteristics by analyzing gamma ray emissions, alpha particle emissions, beta particle emissions, positron emissions, and/or the like. Alternatively or additionally, the particle capture mechanism may apply radiation to excite the dislodged particles and analyze radiation emitted by the one or more dislodged particles. This may comprise applying x-rays; gamma rays; particles, such as neutrons, electrons, and/or positrons; or the like.

The surface particle removal system may comprise a distraction mechanism to prevent the object and/or a person holding the object from realizing the dislodging fluid jet has been delivered to the target location. The distraction mechanism may comprise a speaker. The speaker may be configured to create a masking sound to disguise or drown out the sound of the dislodging fluid jet and/or to create a distracting sound to draw the attention of the object and/or person holding the object. The distraction mechanism may be configured to create a tactile stimulus. The tactile stimulus may be delivered to the target location, so the object mistakes the dislodging fluid jet for the tactile stimulus.

The dislodging fluid jet may be configured to deliver additional substances to the target location. For example, the dislodging fluid jet may comprise an abrasive substance, an adhering substance, or the like. The abrasive substance may be used for various purposes, such as to dislodge particles, to prepare the surface for additional substances, or the like. The adhering substance may also be used for various purposes such as adhering new particles for subsequent removal, adhering to particles on the object, adhering to the dislodged particles, or the like. When the adhering substance is used for adhering to particles, the adhering substance may be further configured to alter the aerodynamic characteristics of the particles, to adhere to the particle capture mechanism to aid in capturing the particles, and/or to aid in dislodging the particles from the object.

The dislodging fluid jet may comprise a tag in some embodiments. The tag may be configured to increase detectability of the object and/or to adhere to the object. The tag may be a magnetic tag, a radio-frequency identification (RFID) tag, a fluorescent dye, and/or the like. Alternatively or additionally, the tag may be configured to increase detectability of the dislodged particles. For example, the tag may be configured to be detectable by an image sensor. The tag may also be configured to adhere to the dislodged particles.

FIG. 1 is a front view of a system 100 for acquiring surface particles from an object for analysis. The system 100 may comprise an image sensor 110 for detecting particles of interest. The image sensor 110 may image a person 160 to detect the particles of interest. The image sensor 110 may image the person's hair 161, skin surface 162, clothing 163, and/or an object, such as a briefcase 164 carried by the person. The image sensor 110 may then select a target location comprising the particles of interest for delivery of a dislodging fluid jet.

A first outlet 120 may deliver the dislodging fluid jet to the target location. A tip 121 of the first outlet 120 may be moved relative to the base 122 to aim the first outlet 120 at the target location. The system 100 may further comprise a second outlet 125 for delivering a deflecting fluid jet. The deflecting fluid jet may impact the dislodging fluid jet in flight to direct the dislodging fluid jet to the target location. In some embodiments, feedback from the image sensor 110 may be used by the first and second outlets 120, 125 to steer the dislodging fluid jet to the target location. The first outlet 120 may continue to deliver the dislodging fluid jet and/or increase the power of the dislodging fluid jet until the particles of interest are dislodged.

Third and fourth outlets 130, 135 may be configured to deliver a capturing fluid jet to direct the dislodged particles to one or more particle capture mechanisms 140. In some embodiments, the image sensor 110 may be further configured to track the dislodged particles in flight. The third and fourth outlets 130, 135 may use tracking information from the image sensor to direct the dislodged particles to the particle capture mechanisms 140. The particle capture mechanisms 140 may then analyze the particles, such as to determine identifying characteristics of the particles. Each particle capture mechanism may be coupled to a different analysis system. Alternatively, a single, larger particle capture mechanism may capture the dislodged particles and/or the particles may be divided after capture for analysis by different analysis systems.

An output device, such as a display device 150, may provide information to an operator of the system 100. For example, the display device 150 may provide information from the image sensor 110 before, during, or after dislodgement of the particles of interest, such as by displaying an image captured by the image sensor. Alternatively or additionally, the display device 150 may provide status information on the outlets 120, 125, 130, 135 and/or particle capture mechanisms 140. The results of analysis by the particle capture mechanisms 140 may also be displayed, such as identifying information of the particles and/or an indication a person is cleared or not cleared.

Figure 2:
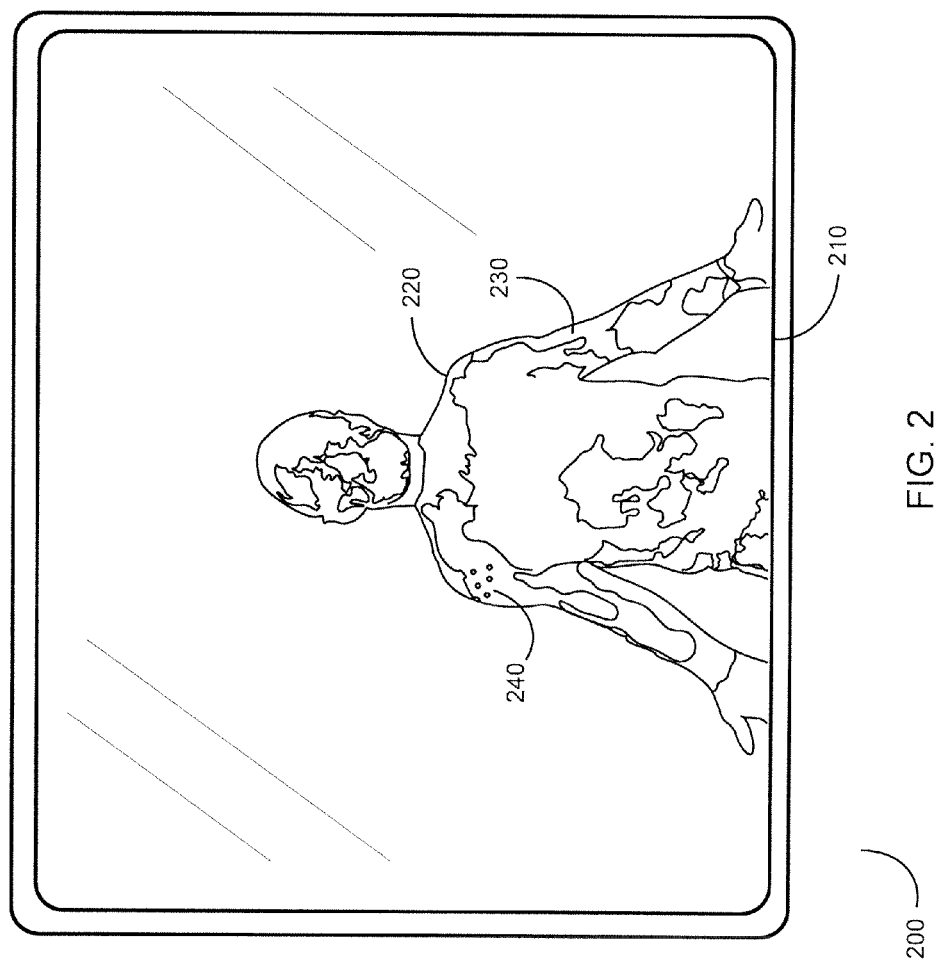
FIG. 2 is an exemplary screen display from a display device.

FIG. 2 is an exemplary screen display 200 from the display device 150. The exemplary screen display 200 comprises an image 210 of a person 220 captured by an image sensor configured to detect electromagnetic radiation in the infrared spectrum. Contour lines 230 and/or various colors may be used to represent the intensities of the infrared radiation received by the image sensor. In some instances, particles of interest 240 may be more easily detected in the infrared spectrum than in other spectrums. In some embodiments, other spectrums may be used to identify particles of interest instead of or in addition to the infrared spectrum. Multiple spectrums may be used synergistically such as by identifying a particle using radiation with a longer wavelength and more precisely locating the particle using radiation with a shorter wavelength. Once identified, the particles of interest may be targeted for dislodgement.

Figure 3:
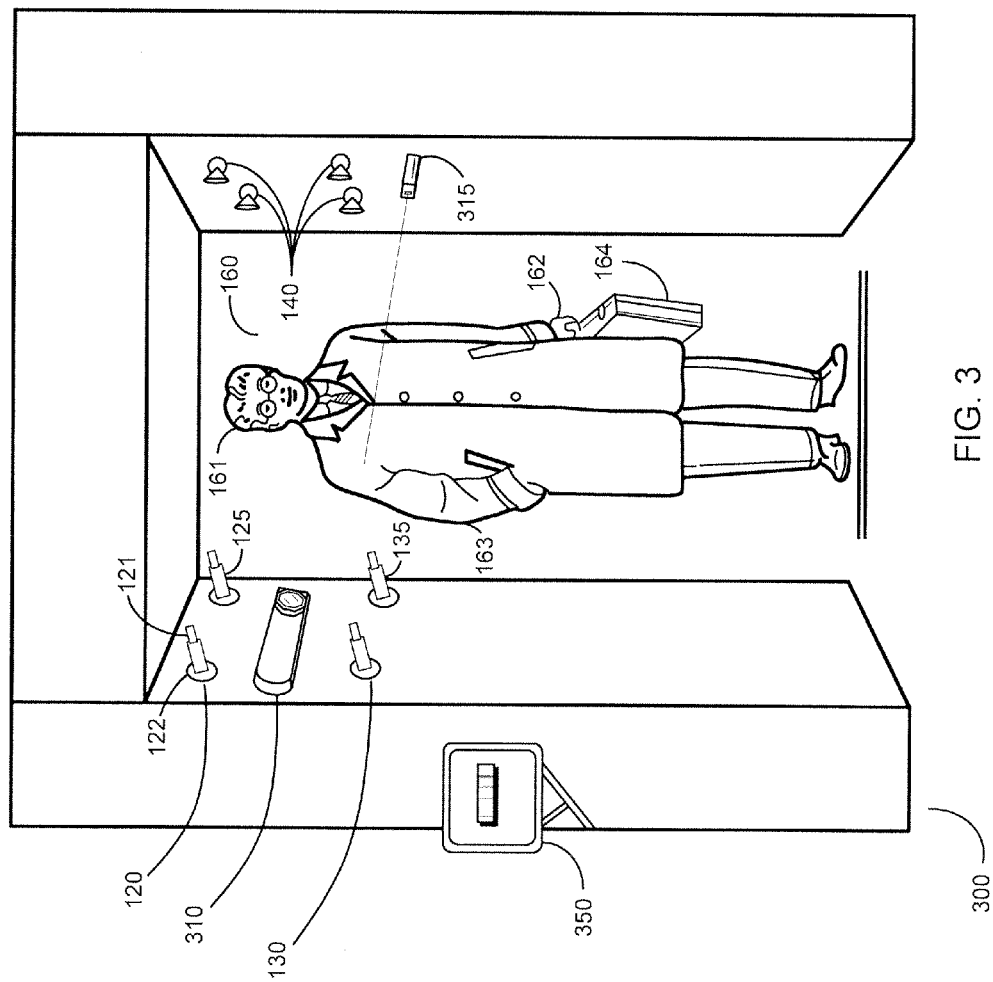
FIG. 3 is a front view of a system that uses spectral emissions to identify particles of interest.

FIG. 3 is a front view of a system 300 that uses spectral emissions to identify particles of interest. In the illustrated embodiment, the system 300 may comprise a laser 315 to spectrally excite the particles of interest. In other embodiments, a different type of light source may be used, such as a collimated beam. An image sensor 310 may comprise a spectrometer that is configured to detect spectral emissions from particles irradiated by the laser. A detected spectral emission spectrum may be displayed on a display device 350. Because different substances produce different spectral emissions spectrums, the detected spectral emission spectrum may be used to identify the composition of the excited particles. If the detected spectral emission spectrum matches the emission spectrum of a substance of interest, the particles may be dislodged and captured for analysis. In other embodiments, a light source may be configured to cause fluorescence of particles of interest, and the image sensor may be configured to detect fluorescence.

Figure 4:
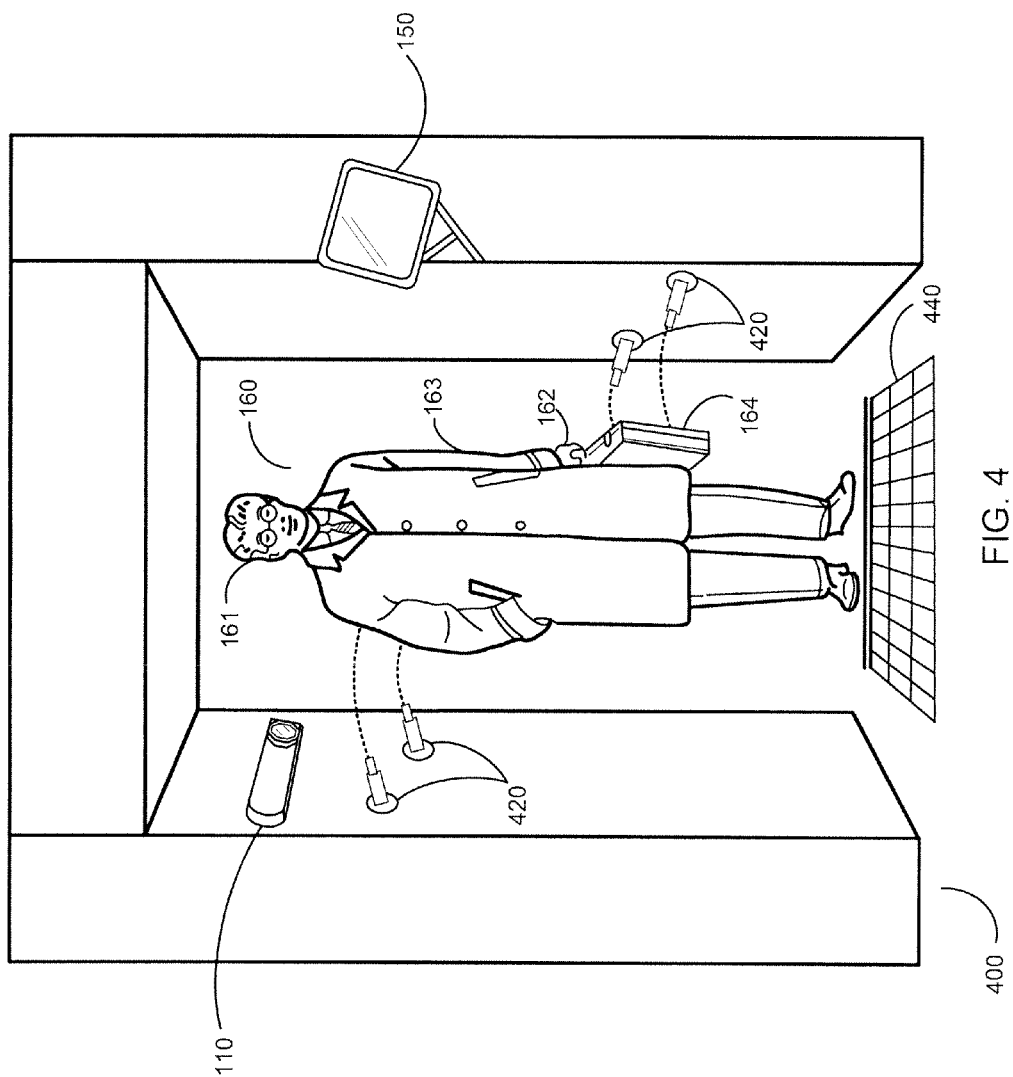
FIG. 4 is a front view of a system configured to deliver one or more dislodging fluid jets comprising a liquid to target locations.

FIG. 4 is a front view of a system 400 configured to deliver one or more dislodging fluid jets comprising a liquid to target locations. A plurality of outlets 420 may be configured to deliver the dislodging fluid jets. In some embodiments, the dislodging fluid jets may be delivered only to inanimate objects, such as clothing 163, a briefcase 164, or the like. The particle capture mechanism 440 for liquid fluid jets may be a grate or the like located below the object. The particle capture mechanism 440 may capture the liquid fluid jets and particles as they drop from the object.

Figure 5:
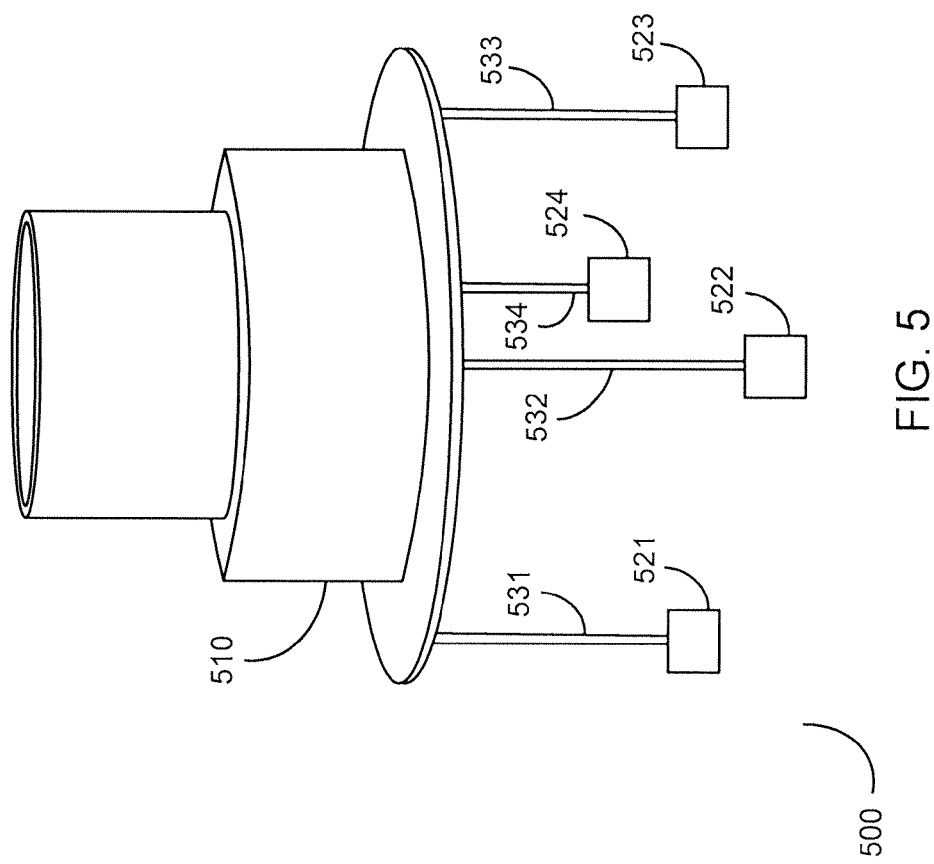

FIG. 5 is a side view of a mechanically controlled outlet 500 for delivering a dislodging fluid jet, a deflecting fluid jet, a capturing fluid jet, or the like. The mechanically controlled outlet 500 may comprise a nozzle 510 for directing the flow of the fluid jet. The nozzle 510 may be aimed such that the dislodging fluid jet is directed towards the target location. A plurality of motors 521, 522, 523, 524 and lead screws 531, 532, 533, 534 may be used to control aiming of the nozzle 510. By adjusting opposing lead screws 531, 532, 533, 534 in opposite directions, the nozzle 510 may be tilted in a desired direction. In other embodiments, there may be more or fewer motors or a different method of mechanical aiming may be used.

Figure 6:
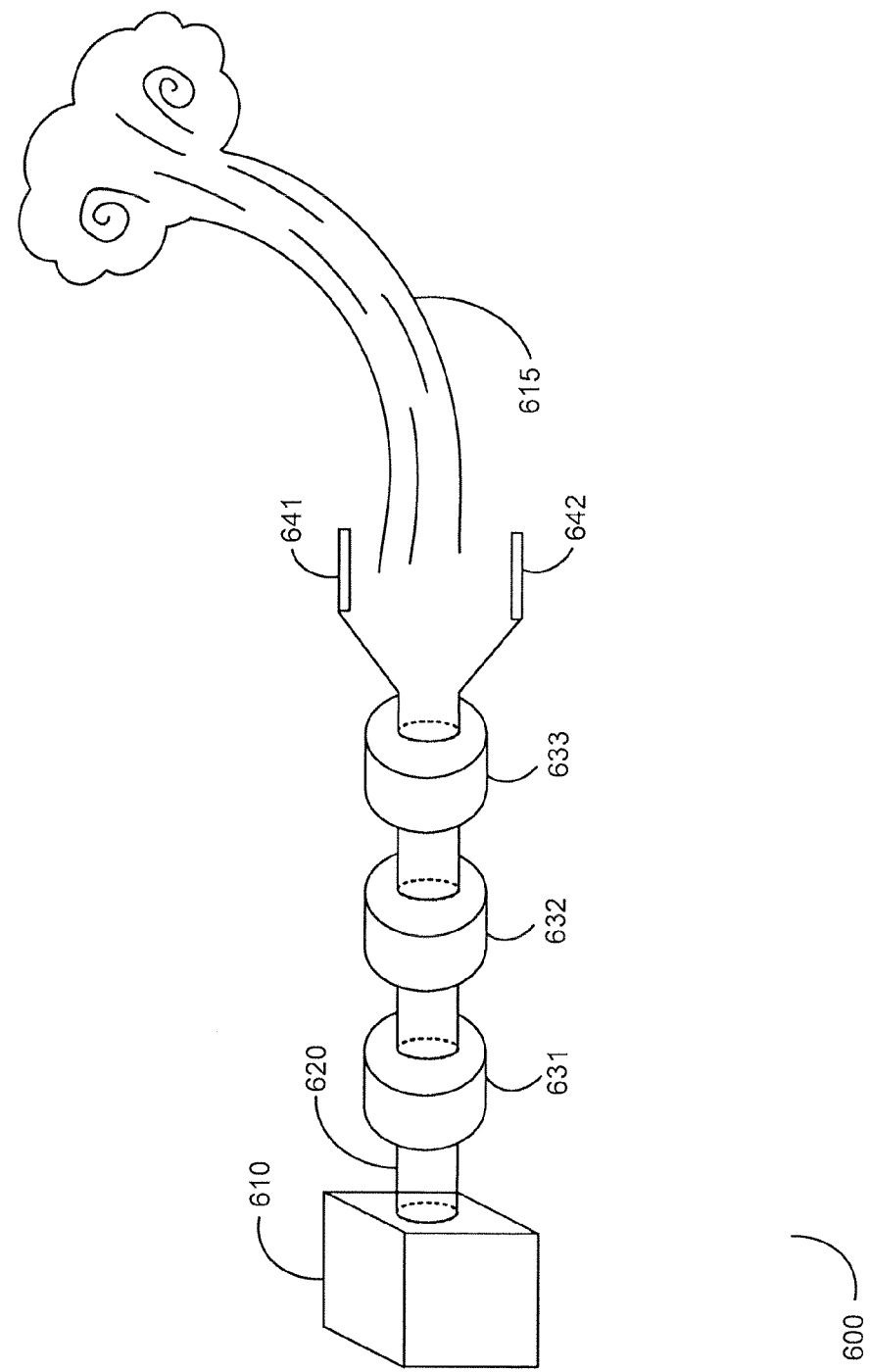

FIG. 6 is a cross-section view of an outlet 600 for electrically steering a dislodging fluid jet, a deflecting fluid jet, a capturing fluid jet, or the like. An ionized fluid source 610 may deliver an ionized fluid jet 615 to a fluid tube 620. A plurality of electromagnets 631, 632, 633 and/or a plurality of charged plates 641, 642 may deflect the ionized fluid jet 615 so that it impinges on the target location. The polarity and strength of the electromagnets 631, 632, 633 and/or the charge on the plates 641, 642 may be altered to change the direction that the ionized fluid jet 615 is deflected. In some embodiments, the electromagnets 631, 632, 633 may control deflection in one dimension and the plates 641, 642 may control deflection in another dimension. In other embodiments, the outlet 600 may comprise only electromagnets 631, 632, 633 or only plates 641, 642.

Figure 7:
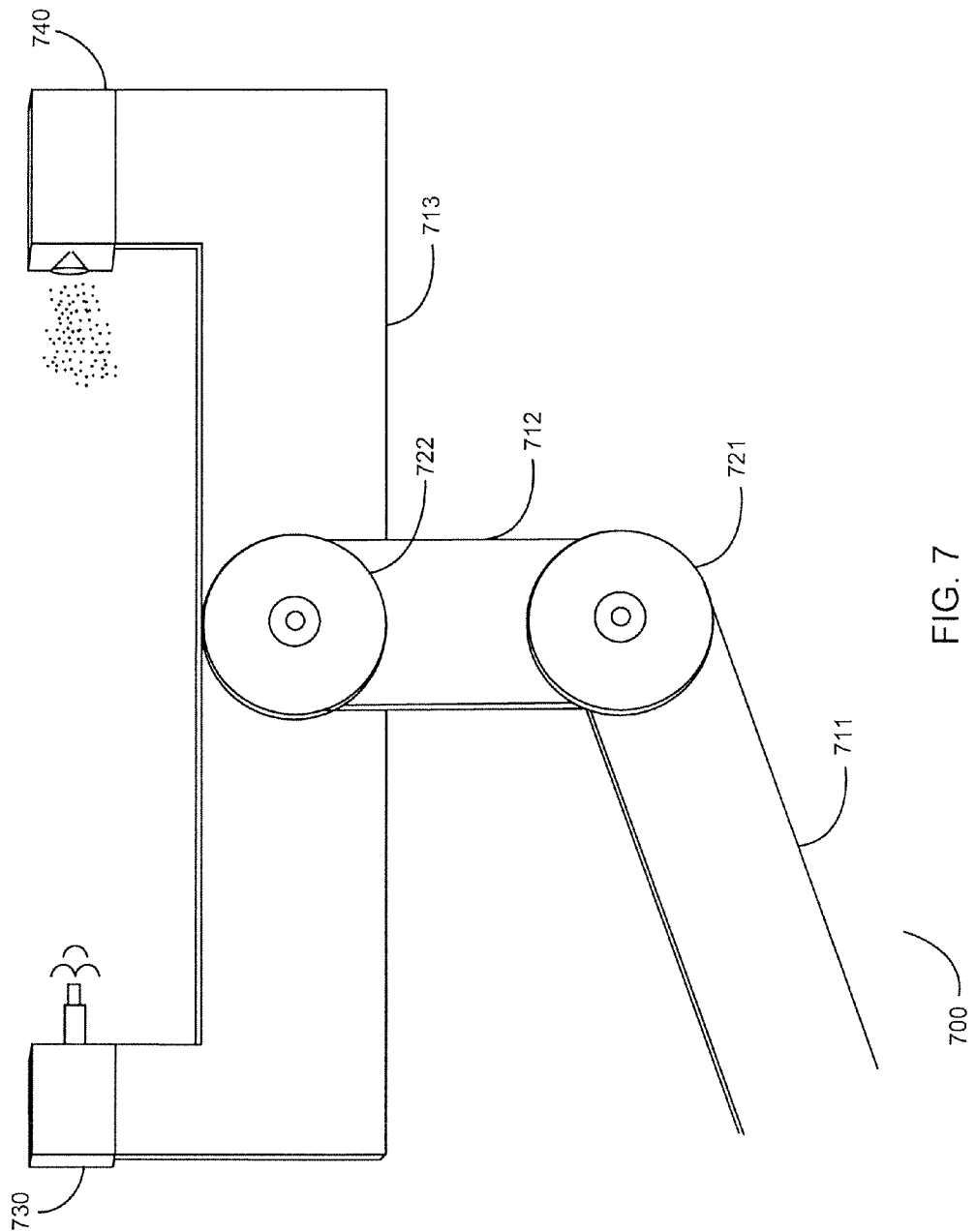
FIG. 7 is a top view of a robotic arm for positioning an outlet for delivering a dislodging fluid jet and a particle capture mechanism for capturing particles dislodged by the dislodging fluid jet.

FIG. 7 is a top view of a robotic arm 700 for positioning an outlet 730 for delivering a dislodging fluid jet and a particle capture mechanism 740 for capturing particles dislodged by the dislodging fluid jet. The robotic arm 700 may comprise multiple segments 711, 712 that may be rotated and positioned using hinges 721, 722. The outlet 730 may be located on a bracket 713 at the end of the arm. This may allow the robotic arm 700 to precisely position the outlet 730. For example, the outlet 730 may be positioned very near particles of interest on an object to increase the likelihood the particles will be dislodged. The particle capture mechanism 740 may be positioned to maximize the probability of capturing the dislodged particles. For example, the particle capture mechanism 740 may be in the path of the dislodging fluid jet, so that it will capture dislodged particles entrained in the dislodging fluid jet. Alternatively or additionally, the particle capture mechanism 740 may be positioned in an anticipated path of the dislodged particles and/or the robotic arm 700 may adjust the position of the particle capture mechanism 740 based on feedback from an image sensor (not shown).

Figure 8:
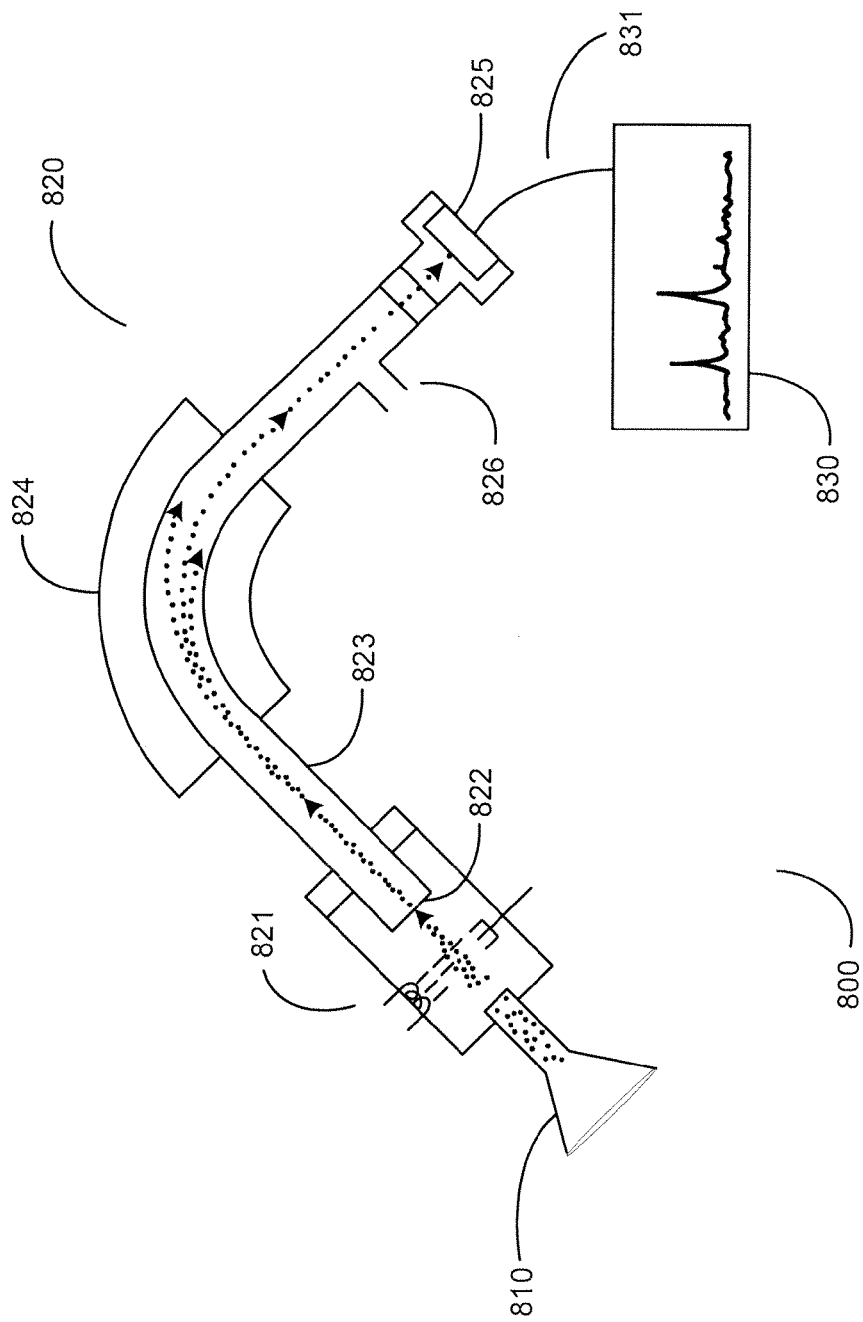
FIG. 8 is a schematic diagram of a particle capture mechanism configured to analyze captured particles with a mass spectrometer.

FIG. 8 is a schematic diagram of a particle capture mechanism 800 configured to analyze captured particles with a mass spectrometer 820. A capture interface 810 may capture dislodged particles. The dislodged particles may be bombarded with an electron beam 821 to ionize the particles. A voltage may be applied to an accelerator plate 822 to accelerate the ionized particles into a flight tube 823. A magnet 824 may bend the path of the ionized particles based on the particles' masses. Lighter particles may bend more than heavier particles.

One or more detectors 825 may determine the mass of the particles based on which detector 825 the particles enter. In some embodiments, the detectors 825 may be configured to only detect particles of interest. In other embodiments, the detectors 825 may detect particles with a plurality of masses, including particles that are not of interest. A vacuum outlet 826 may allow air and other substances that might interfere with the ionized particles to be removed from the flight tube 823. A wire 831 may be used to convey the detection information to a display 830. The display 830 may visually depict the detected masses, identify the particles from the detected masses, and/or indicate whether a person is cleared or not.

Figure 9:
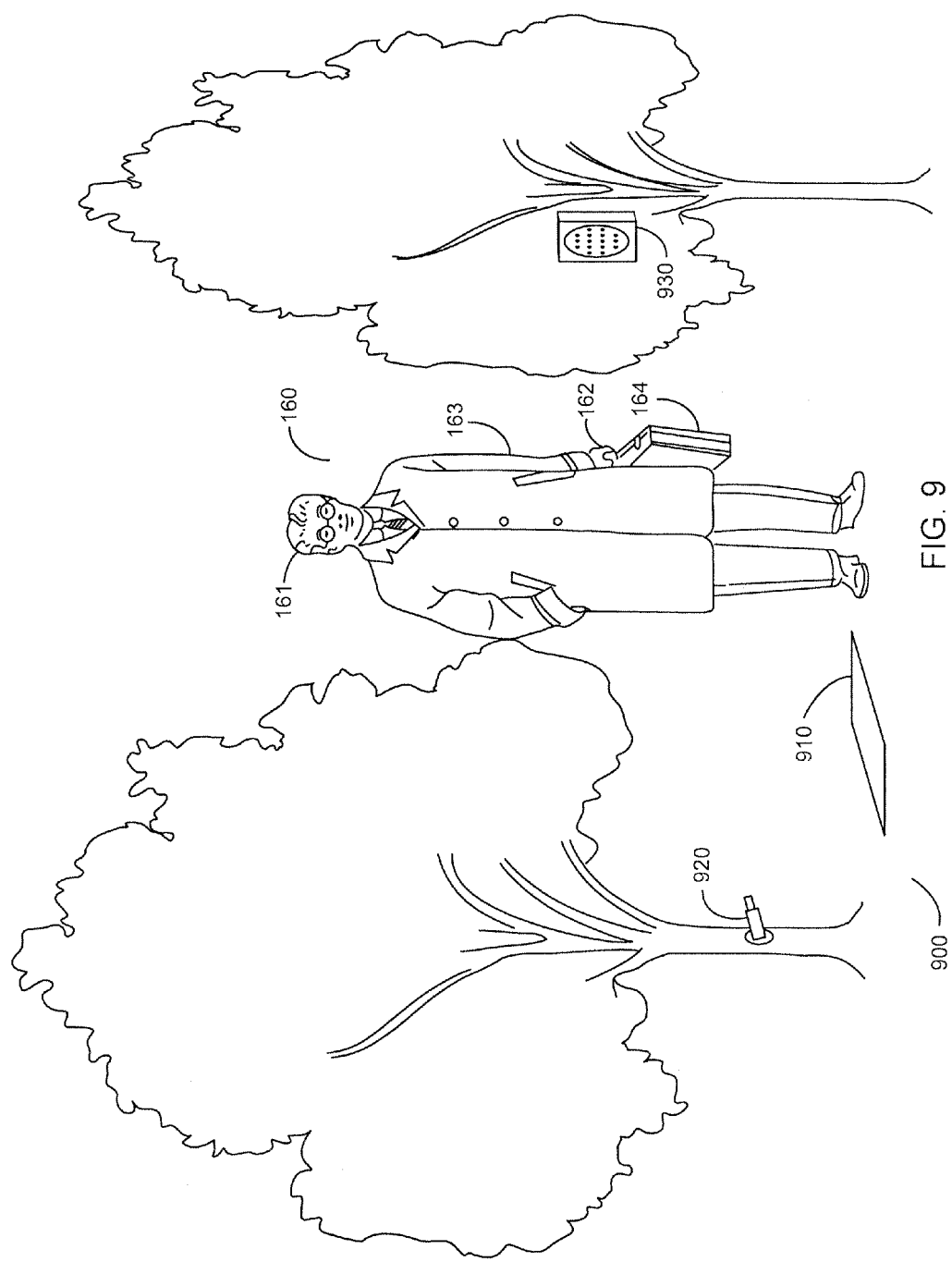
FIG. 9 is a front view of a system for dislodging particles from an object.

FIG. 9 is a front view of a system 900 for dislodging particles from an object. The system 900 may comprise a proximity sensor 910 configured to detect the presence of a person 160. For example, the proximity sensor 910 may be a pressure sensor configured to detect weight from the person 160 on the proximity sensor 910, an optical sensor (e.g., infrared), or the like. An outlet 920 may be configured to deliver a dislodging fluid jet after the person 160 is detected. The proximity sensor 910 may be located in a delivery region of the outlet 920, so the dislodging fluid jet can be delivered to the person 160 when the person 160 is detected by the proximity sensor 910. The outlet 920 may be discreetly positioned so that it is not easily noticed by passersby.

A speaker 930 may be configured to create a distracting sound when the dislodging fluid jet is delivered. The speaker 930 may be located on an opposite side of the person 160 from the outlet 920 to draw attention away from the outlet. The speaker 930 may create a loud sound, a startling sound, and/or an attention-grabbing sound likely to distract the person 160. Alternatively or additionally, the speaker 930 may create a masking sound, so the person does not hear and/or notice the sound of the outlet 920 delivering the dislodging fluid jet. The masking sound may be configured to have frequency components similar to the sound of delivery of the dislodging fluid jet to make the sounds hard to distinguish. The speaker 930 may be positioned near the outlet 920 when the speaker 930 is configured to make a masking sound.

Figure 10:
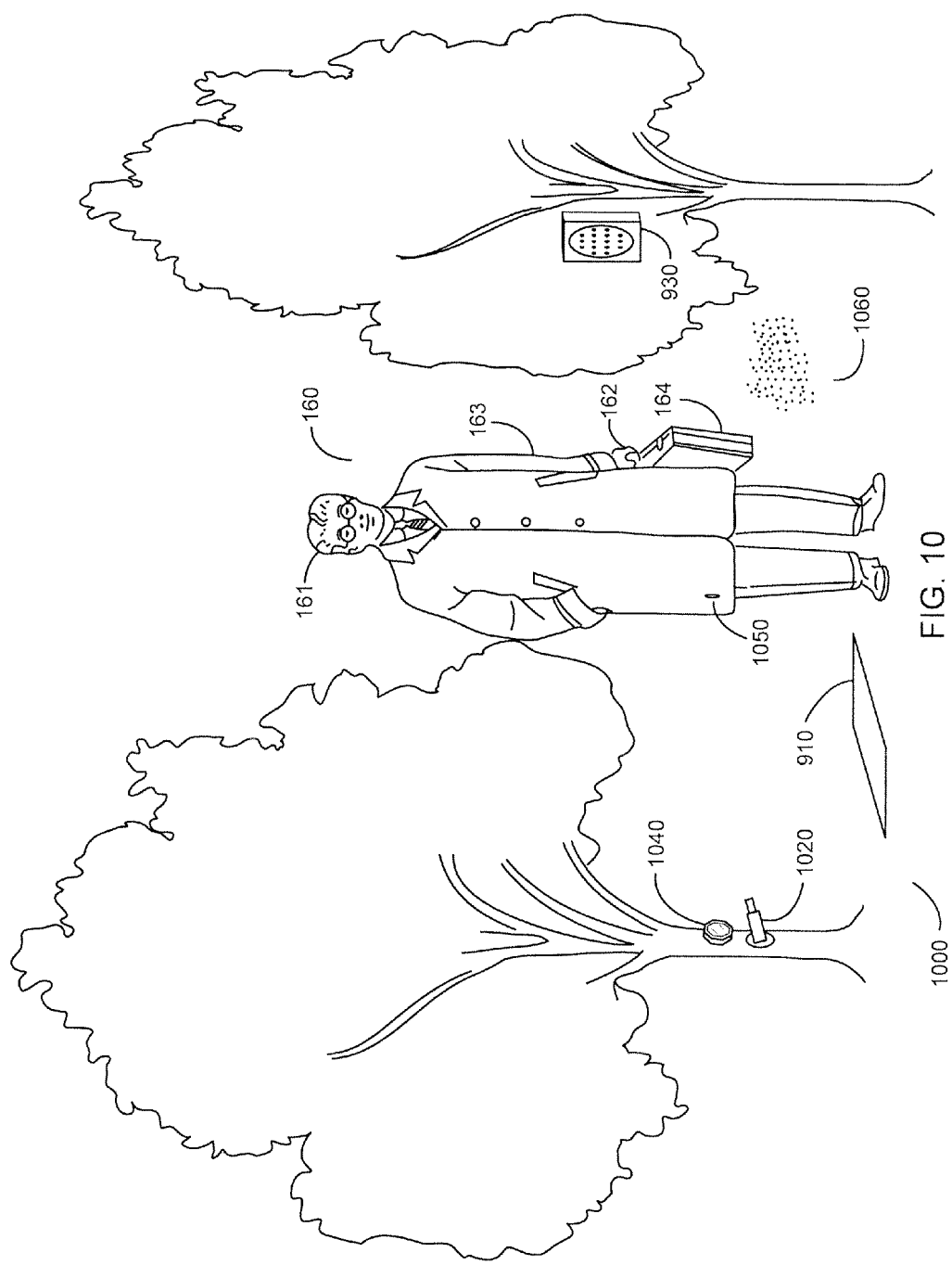
FIG. 10 is a front view of a system for dislodging particles from an object that is further configured to track and/or analyze particles dislodged from the object.

FIG. 10 is a front view of a system 1000 for dislodging particles from an object that is further configured to track and/or analyze particles 1060 dislodged from the object. The system 1000 may comprise an image sensor 1040 configured to track and/or analyze the dislodged particles 1060. The image sensor 1040 may track a fluorescence pattern, a light scattering pattern, spectral emissions, and/or the like from the dislodged particles 1060. The image sensor 1040 may analyze electromagnetic radiation in the infrared spectrum, visible spectrum, ultraviolet spectrum, or the like. The image sensor 1040 may further comprise a light source (not shown) to aid in tracking and/or analyzing the dislodged particles 1060. In some embodiments, the image sensor 1040 may also be configured to sense proximity of the person 160 rather than the proximity sensor 910 sensing the proximity.

The system 1000 may comprise an outlet 1020 configured to deliver an RFID tag 1050 in addition to a dislodging fluid jet. The RFID tag 1050 may be configured to adhere to and/or grasp clothing 163 of the person 160. The RFID tag 1050 may allow the person 160 to be identified from a distance. For example, some types of analysis may take time to process, and the person 160 may have left before the analysis is complete. The RFID tag 1050 may then be used to locate the person 160 if the results of the analysis indicate the dislodged particles 1060 are particles of interest. The outlet 1020 may be further configured to deliver a substance configured to increase the detectability of and/or react with the dislodged particles 1060, which may aid in tracking, identifying, and/or analyzing the dislodged particles 1060.

It will be understood by those having skill in the art that many changes may be made to the details of the above-described embodiments without departing from the underlying principles of the disclosure. The scope of the present disclosure should, therefore, be determined only by the following claims.

The invention claimed is:

1. A system for acquiring surface particles from an object for analysis, the system comprising:
    an image sensor configured to determine a target location on the object;
    a first outlet configured to deliver a dislodging fluid jet;
    a steering mechanism configured to steer the dislodging fluid jet to the target location, wherein the steering mechanism is configured to steer the dislodging fluid jet in flight by altering the path of the dislodging fluid jet, and wherein the steering mechanism comprises a charged element to deflect an ionized fluid; and
    a particle capture mechanism configured to capture one or more particles dislodged from the target location.

2. The system of claim 1, wherein the image sensor is configured to determine a target location by identifying one or more particles of interest on the object.

3. The system of claim 2, wherein the image sensor is configured to detect electromagnetic radiation.

4. The system of claim 3, wherein the image sensor comprises a camera.

5. The system of claim 3, wherein the image sensor is configured to detect electromagnetic radiation in the terahertz spectrum.

6. The system of claim 3, wherein the image sensor is configured to detect electromagnetic radiation in the infrared spectrum.

7. The system of claim 3, wherein the image sensor is configured to detect electromagnetic radiation in the visible spectrum.

8. The system of claim 3, wherein the image sensor is configured to detect electromagnetic radiation in the ultraviolet spectrum.

9. The system of claim 3, wherein the image sensor is configured to detect electromagnetic radiation in the x-ray spectrum.

10. The system of claim 3, further comprising an electromagnetic radiation emitter.

11. The system of claim 10, wherein the electromagnetic radiation emitter comprises a light source.

12. The system of claim 3, wherein the image sensor comprises a spectrometer.

13. The system of claim 3, wherein the image sensor is configured to detect fluorescent emissions.

14. The system of claim 2, further comprising an ultrasonic wave emitter, wherein the image sensor is configured to detect ultrasonic waves.

15. The system of claim 1, wherein the steering mechanism is configured to aim the first outlet.

16. The system of claim 15, wherein the steering mechanism comprises a motor.

17. The system of claim 15, wherein the steering mechanism comprises a robotically movable arm.

18. The system of claim 1, wherein the steering mechanism further comprises a second outlet configured to deliver a deflecting fluid jet to deflect the path of the dislodging fluid jet.

19. The system of claim 1, wherein the steering mechanism is configured to mechanically steer the dislodging fluid jet.

20. A non-transitory computer-readable storage medium comprising program code for performing a method for acquiring surface particles from an object for analysis, the method comprising:
   determining a target location on the object;
   delivering a dislodging fluid jet from a first location;
   steering the dislodging fluid jet to the target location; and
   capturing one or more particles dislodged from the target location for analysis, wherein capturing comprises opening a gate of a particle capture mechanism upon arrival of the one or more dislodged particles.

21. The non-transitory computer-readable storage medium of claim 20, wherein capturing comprises suctioning the one or more dislodged particles.

22. The non-transitory computer-readable storage medium of claim 20, wherein capturing comprises capturing the one or more dislodged particles with an electrostatic precipitator.

23. The non-transitory computer-readable storage medium of claim 20, wherein capturing comprises capturing the one or more dislodged particles with a filter.

24. The non-transitory computer-readable storage medium of claim 20, wherein the method further comprises tracking the one or more dislodged particles after dislodgement from the object.

25. The non-transitory computer-readable storage medium of claim 24, wherein the method further comprises predicting a path of the one or more dislodged particles.

26. The non-transitory computer-readable storage medium of claim 24, wherein the method further comprises predicting an arrival time of the one or more dislodged particles at a particle capture mechanism.

27. The non-transitory computer-readable storage medium of claim 24, wherein the method further comprises steering the one or more dislodged particles by delivering a capturing fluid jet from a second location to steer the one or more dislodged particles.

28. The non-transitory computer-readable storage medium of claim 24, wherein capturing the one or more dislodged particles comprises intercepting a path of the one or more dislodged particles with a robotically movable arm.

29. The non-transitory computer-readable storage medium of claim 20, wherein the method further comprises analyzing biological characteristics of the one or more dislodged particles.

30. The non-transitory computer-readable storage medium of claim 20, wherein the method further comprises analyzing chemical characteristics of the one or more dislodged particles.

31. The non-transitory computer-readable storage medium of claim 20, wherein the method further comprises analyzing radioactive characteristics of the one or more dislodged particles.

32. The non-transitory computer-readable storage medium of claim 20, wherein the method further comprises analyzing fluorescence of the one or more dislodged particles.

33. The non-transitory computer-readable storage medium of claim 20, wherein the method further comprises analyzing spectral emissions of the one or more dislodged particles.

34. The non-transitory computer-readable storage medium of claim 20, wherein the method further comprises analyzing the one or more dislodged particles with a mass spectrometer.

35. A method of acquiring surface particles from an object for analysis, the method comprising:
   determining a target location on the object by identifying one or more particles of interest;
   delivering a dislodging fluid jet from a first location;
   steering the dislodging fluid jet to the target location; and
   capturing one or more particles dislodged from the target location for analysis, wherein capturing comprises opening a gate of a particle capture mechanism upon arrival of the one or more dislodged particles.

36. A method of acquiring surface particles from an object for analysis, the method comprising:
   determining a target location on the object by identifying one or more particles of interest;
   delivering a dislodging fluid jet from a first location;
   steering the dislodging fluid jet to the target location using a steering mechanism to steer the dislodging fluid jet in flight by altering the path of the dislodging fluid jet, wherein steering the dislodging fluid jet comprises steering using a charged element to deflect the dislodging fluid jet comprising an ionized fluid; and
   capturing one or more particles dislodged from the target location.

37. The method of claim 36, wherein steering the dislodging fluid jet further comprises steering by delivering a deflecting fluid jet from a second location to deflect the path of the dislodging fluid jet.

38. A system for of acquiring surface particles from an object for analysis, the system comprising:
   an image sensor configured to determine a target location on the object;
   a first outlet configured to deliver a dislodging fluid jet from a first location;
   a steering mechanism configured to steer the dislodging fluid jet to the target location; and
   a particle capture mechanism configured to capture one or more particles dislodged from the target location for analysis, wherein the particle capture mechanism is configured to capture the one or more dislodged particles by opening a gate of a particle capture mechanism upon arrival of the one or more dislodged particles.

* * * * *